US011097054B2

(12) United States Patent
Orofino (10) Patent No.: US 11,097,054 B2
(45) Date of Patent: Aug. 24, 2021

(54) CARTRIDGE WITH FLEXIBLE BAG FOR INJECTING A PHARMACEUTICAL SOLUTION AND METHOD FOR MANUFACTURING THE CARTRIDGE

(71) Applicant: OROFINO PHARMACEUTICALS GROUP S.R.L., Rome (IT)

(72) Inventor: Ernesto Orofino, Rome (IT)

(73) Assignee: OROFINO PHARMACEUTICALS GROUP S.R.L., Rome (IT)

( * ) Notice: Subject to any disclaimer, the term of this patent is extended or adjusted under 35 U.S.C. 154(b) by 299 days.

(21) Appl. No.: 16/076,908

(22) PCT Filed: Jan. 12, 2017

(86) PCT No.: PCT/IB2017/050152
§ 371 (c)(1),
(2) Date: Aug. 9, 2018

(87) PCT Pub. No.: WO2017/137854
PCT Pub. Date: Aug. 17, 2017

(65) Prior Publication Data
US 2019/0046730 A1    Feb. 14, 2019

(30) Foreign Application Priority Data
Feb. 10, 2016    (IT) .................. 102016000013599

(51) Int. Cl.
*A61M 5/00*    (2006.01)
*A61M 5/24*    (2006.01)
(Continued)

(52) U.S. Cl.
CPC ............ *A61M 5/2448* (2013.01); *A61J 1/067* (2013.01); *A61J 1/10* (2013.01); *A61M 5/002* (2013.01);
(Continued)

(58) Field of Classification Search
CPC .. A61M 5/2448; A61M 5/002; A61M 5/2425; A61M 5/282; A61J 1/067;
(Continued)

(56) References Cited

U.S. PATENT DOCUMENTS 4,312,344 A *   1/1982   Nilson ............... A61M 5/31511
                                                            604/212
2001/0047162 A1   11/2001   Yugari
(Continued)

FOREIGN PATENT DOCUMENTS

EP    2 796 157 A1    10/2014
GB    1 573 514 A      8/1980
(Continued)

OTHER PUBLICATIONS

International Search Report and Written Opinion of the International Searching Authority for International Patent Application No. PCT/IB2017/050152 dated Jul. 26, 2017, 15 pages.

*Primary Examiner* — Nathan R Price
*Assistant Examiner* — Tania Ismail
(74) *Attorney, Agent, or Firm* — Merchant & Gould P.C.

(57) ABSTRACT

A cartridge (10) for injecting a pharmaceutical solution includes at least one flexible small bag (18, 22) made of thin film walls, having a chamber (12, 14) containing a pharmaceutical substance (S, P, L) and having a head surface (37) being outwardly convex. A syringe (100) for injecting a pharmaceutical solution (S) includes a body (102) extended along a main axis (X), an accommodating space (120) to accommodate a cartridge (10), and a plunger (110) with a head (113) being dome-shaped and convex towards the space (120), preferably asymmetrical with respect to the main axis (X). An injection kit for injecting a pharmaceutical solution including a syringe (100) and at least one cartridge (100).

10 Claims, 6 Drawing Sheets

(51) Int. Cl.
*A61J 1/06* (2006.01)
*A61J 1/10* (2006.01)
A61M 5/315 (2006.01)
A61J 1/16 (2006.01)
A61M 1/00 (2006.01)
A61M 5/20 (2006.01)
A61J 1/14 (2006.01)

(52) U.S. Cl.
CPC .......... *A61M 5/2425* (2013.01); *A61J 1/1437* (2013.01); *A61J 1/1481* (2015.05); *A61J 1/16* (2013.01); *A61M 1/0009* (2013.01); *A61M 5/2066* (2013.01); *A61M 2005/2451* (2013.01); *A61M 2005/31516* (2013.01); *A61M 2205/0238* (2013.01); *A61M 2205/123* (2013.01); *A61M 2207/00* (2013.01); *A61M 2207/10* (2013.01)

(58) Field of Classification Search
CPC .......... A61J 1/10; A61J 1/1437; A61J 1/1481; A61J 1/16
See application file for complete search history.

(56) References Cited

U.S. PATENT DOCUMENTS

2009/0024104 A1* 1/2009 Keller ................ A61M 5/2459
604/411
2013/0211248 A1* 8/2013 Cowan ................ A61M 5/1452
600/432

FOREIGN PATENT DOCUMENTS

| WO | 81/02838 A1 | 10/1981 |
| WO | 2011/068130 A1 | 6/2011 |
| WO | 2012/061140 A1 | 5/2012 |

\* cited by examiner

CARTRIDGE WITH FLEXIBLE BAG FOR INJECTING A PHARMACEUTICAL SOLUTION AND METHOD FOR MANUFACTURING THE CARTRIDGE

This application is a National Stage Application of PCT/IB2017/050152, filed 12 Jan. 2017, which claims benefit of Ser. No. 102016000013599, filed 10 Feb. 2016 in Italy, and which applications are incorporated herein by reference. To the extent appropriate, a claim of priority is made to each of the above-disclosed applications.

BACKGROUND OF THE INVENTION

The present invention refers to the technical sector of the syringes for injecting pharmaceutical products.

Presently, the sterile powder raw materials are mainly packed by the producers of active substances, in aluminium containers or in plastic bags, usually made of polyethylene.

In order to sell them, producers have demonstrated that each one of the raw materials, on top of preserving sterility, remains stable inside containers or employed bags for a given period of time; in other words, such powders do not degrade for a definite number of years if they are kept in such containers or bags.

The sterile raw materials are sold to the producers of the final pharmaceutical product, who provide to divide them by means of prior art technologies, placing on the market the final product in the form of sterile powder contained in a bottle. The bottle is complemented by a glass phial containing the solvent.

The use of fine materials for the phial (glass), of compatible materials for the sterile powder, the use of disposable syringes make such system be altogether very expensive.

It is well known in the field the use of syringes provided with a space for accomodating a cartridge, made of flexible material, containing pharmaceutical substances that are kept separated by a proper breakable wall until when they are used. An example of such known devices is disclosed in patent US2001/0047162. However, such prior art devices have some drawbacks: as a matter of fact, due to the accumulation and the stasis of the mixture or of the pharmaceutical substance at the corners of the cartridge, not all the dose is released. This makes the dosing of the actually injected substance imprecise and not much reliable.

SUMMARY OF THE INVENTION

The object of the present invention is to solve the prior art problems taking into consideration the sector's requirements.

In particular, the object of the present invention is supplying a system for releasing pharmaceutical substances reaching high dosage precision by means of a simple and cheap system.

BRIEF DESCRIPTION OF THE DRAWINGS

The characteristics and the advantages of the cartridge, of the syringe and of the method according to the present invention will be cleared by the hereinafter description, by way of non-limiting example, according to the enclosed drawings, wherein.

DETAIL DESCRIPTION OF THE PREFERRED EMBODIMENTS

According to the enclosed Figures, a cartridge 10 includes at least a chamber 12, 14 containing at least a pharmaceutical substance S, P, L.

Figure 11:
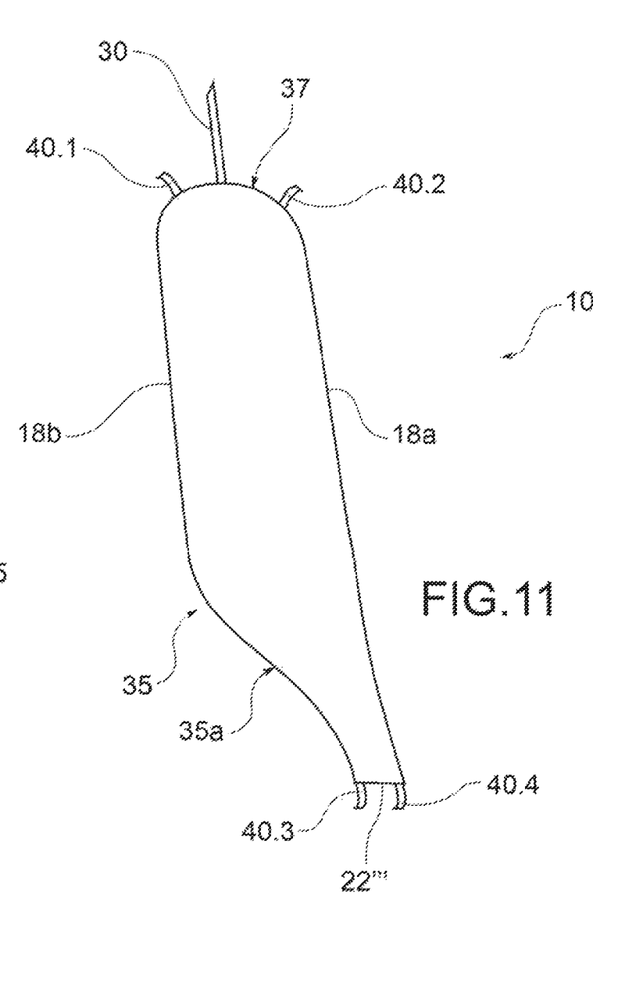
FIGS. 11 and 12 show additional embodiments of a cartridge according to the invention.
Figure 12:
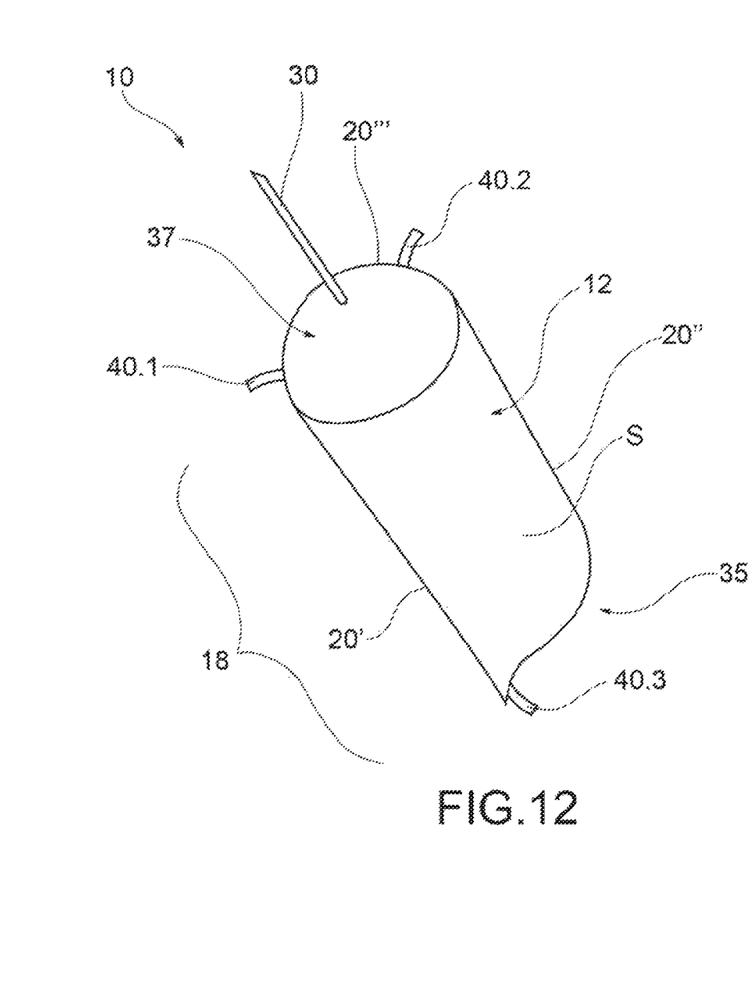

According to the embodiment variant of FIGS. 11 and 12, the cartridge 10 includes a single chamber 12 containing an injectable solution S.

Figure 1A:
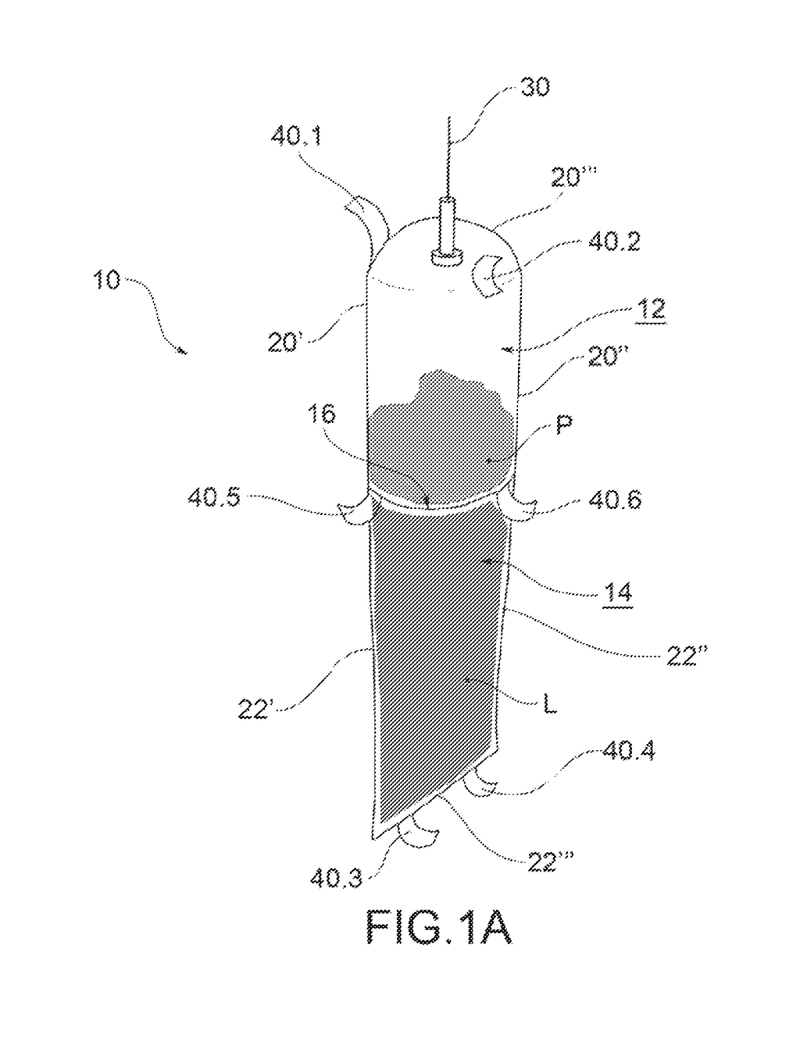
FIGS. 1A and 1B show a respectively axonometric and side view of a cartridge according to one embodiment of the present invention.
Figure 1B:
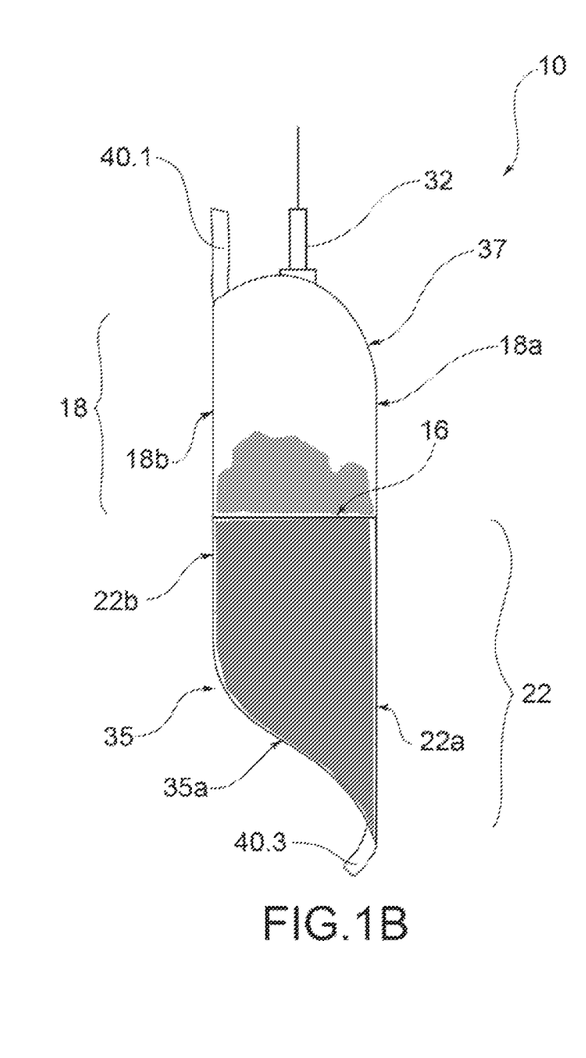

According to the embodiment variant of FIG. 1, the cartridge 10 includes a first chamber 12 or front chamber and a second chamber 14, or back chamber, divided by a breakable dividing wall 16.

As shown in FIG. 1, each chamber 12, 14 contains one of the components of the injectable solution S; for example, the first chamber 12 contains the sterile pharmacological powder P and the second chamber contains a liquid L, typically a solvent or an additional pharmaceutical active ingredient. For example, the sterile pharmacological powder P is a crystal powder or a powder obtained in bulk from the freeze-drying of a solution.

The cartridge 10 is made of thin film walls. Monolayer or multilayer films are usually made of plastic material, preferably polyethylene. In the case of multilayer film, the polyethylene layer is the inner layer, that is the layer contacting the pharmaceutical product.

The cartridge 10 includes at least a small bag 18, 22 that encloses the chamber 12, 14; the small bag 18, 22 is composed of a first lateral wall 18a, 22a being formed by a film and a second lateral wall 18b, 22b facing and opposing the first lateral wall.

According to the variant of FIG. 1, the cartridge 10 includes a first small bag 18 or front small bag, enclosing the first chamber 12; the first small bag 18 is composed of a first lateral wall 18a formed by a film and by a second lateral wall 18b, facing and opposing the first lateral wall 18a.

Preferably, the first wall 18a is joined through joining edges to the second lateral wall 18b, for example along lateral edges 20', 20" and along a front edge 20''', e.g. through welding or bonding. As an alternative, between the first and the second wall additional sides or a film bottom wall are disposed, duly joined to the lateral walls through joining edges for welding or bonding.

Similarly, the cartridge 10 includes a second small bag 22, or back small bag, that encloses the second chamber 14; the second small bag 22 is composed of a first lateral wall 22a being formed by a film and a second lateral wall 22b facing and opposing the first lateral wall 22a.

Preferably, the first wall 22a is joined through joining edges to the second lateral wall 22b, for example along lateral edges 22', 22" and along a back edge 22''', e.g. through welding or bonding. As an alternative, between the first and the second wall additional sides or a film bottom wall are disposed, duly joined to the lateral walls through joining edges for welding or bonding.

Preferably, the cartridge 10 includes a needle for injection 30, applied to the small bag for example so as to protrude from the front edge 20''''. Preferably, the needle 30 is linked to the small bag by means of a needle-carrying component 32.

According to the variant of FIG. 1, the breakable dividing wall 16 is arranged between the first chamber 12 and the second chamber 14. For example, said dividing wall is obtained through an additional welding between the lateral walls 18a, 18b of the first chamber 12 or the lateral walls 22a, 22b of the second chamber, realized so as to separate the chambers 12, 14. Alternatively, said dividing wall is realized by an additional film wall duly joined to the lateral walls of the small bags 18, 22.

Preferably, on the side opposite to the needle 30, the cartridge 10 has a bottom 35 intended to contact a head 113 of a plunger 110 which will be described hereinafter.

Preferably, when the cartridge 10 is in the undeformed condition, the bottom 35 has an outwardly bend 35a, typically outwardly concave, to ease the squeezing of the little bag and the complete emptying thereof.

Preferably, the bend 35a is asymmetrical and formed by the bottom 35 narrowing towards one side of the small bag, collapsing in the back edge 22''''. Such a "whistle" conformation of the bottom 35 facilitates the sliding of the plunger 110.

Preferably, the cartridge 10 has a head surface 37, from which the needle 30 protrudes, outwardly convex. For example, the head surface 37 is dome-shaped. Such dome-shaped conformation of the head 37 facilitates the emptying of the small bag. In fact, since it does not have corners or inlets, no accumulation or stasis of the mixture or of the pharmaceutical substance remains in the little bag that is completely emptied.

Preferably, the head surface 37 is asymmetrical with respect to the main axis X, and it narrows starting from one of the small bag sides. Such a conformation allows a preferential squeezing on a side of the cartridge thus facilitating the emptying of the small bag.

Preferably, the shape of the head surface 37 is complementary to the shape of the head 113 of the plunger 110 and to the shape of the bottom 122 of the distal end 106 of the syringe 100. Such a conformation allows a complete squeezing of the cartridge.

The cartridge 10 is also equipped with engaging means adapted to perform the mechanical engagement of said cartridge with a syringe 100, better described hereinafter.

Preferably, the engaging means include a plurality of engaging elements 40.i protruding from the small bag.

For example, the cartridge 10 is provided with a pair of upper engaging elements 40.1, 40.2 of said engaging means protruding from the first small bag, for example each one from the respective lateral wall 18b, 18a or from the front edge 20''''.

Preferably, the cartridge 10 is also provided with a pair of lower engaging elements 40.3, 40.4 of said engaging means protruding from the second small bag, for example each one from the respective lateral wall 22b, 22a or from the back edge 22''''.

Preferably, the cartridge 10 is also provided with a pair of intermediate engaging elements 40.5, 40.6 of said engaging means protruding in correspondence of the dividing wall 16 separating the two chambers 12, 14.

Figures 2A, 2B:
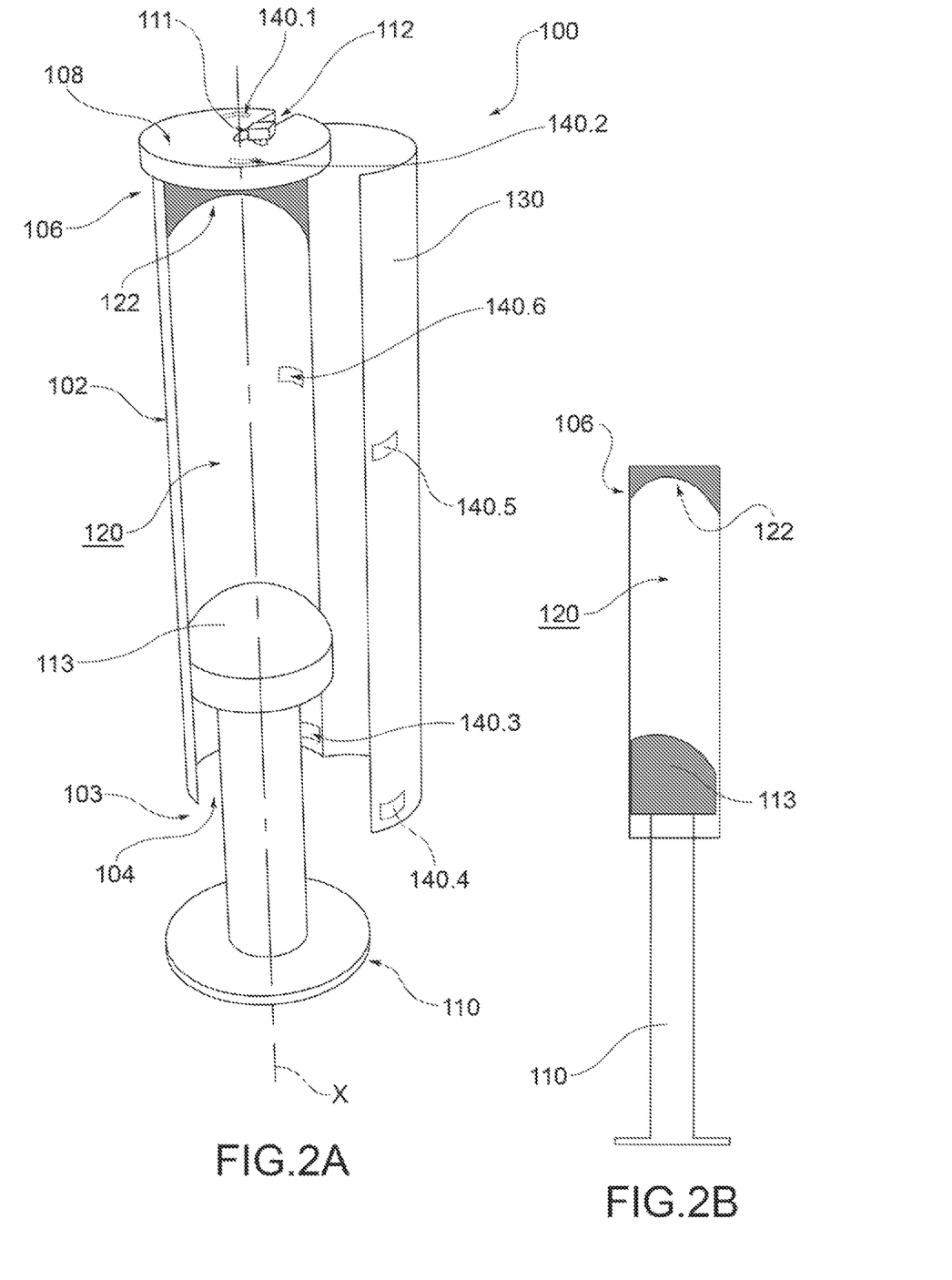
FIGS. 2A and 2B show a respectively axonometric and side view of a syringe for the cartridge of FIG. 1.

The invention also provides for a syringe 100 for the cartridge 10, according to the embodiment shown in FIG. 2.

The syringe 100 includes a body 102, for example tubular, typically having cylindrical shape, predominantly extending along a main axis X between a proximal end 103 where there is a proximal opening 104, and an opposite distal end 106 where a basis 108 of the tubular body 102 is arranged, for example applied to the latter.

The syringe 100 also includes a plunger 110 carrying a head 113 that can be inserted in the tubular body through the proximal opening 104 and sliding inside said tubular body 102 by pushing on the plunger.

The tubular body 100 has an internal accomodating space 120 accessible by opening a mobile wall 130 of said tubular body 102 and adapted to accommodate the cartridge 10, in a starting configuration of the syringe 100.

The syringe 100 is equipped with counter-engaging means adapted to engage mechanically with the engaging means of the cartridge to block the mutual arrangement between the cartridge 10 and the syringe 100.

For example, said counter-engaging means include a plurality of passing-through holes 140.i; said engaging elements 40.i of the cartridge 10 are adapted to be inserted in said holes 140.i and blocked to them.

For example the counter-engaging means include retaining walls adapted to engage with engaging elements 40.i typically inserted in the holes 140.i in order to block them to the syringe. For example, sliding or rotating or implanting walls are provided, being usually able to close the passing-through holes, so that, by closing the holes 140.i, they hold the engaging elements 40.i.

According to an alternative embodiment, on the cartridge external wall, blocking snap-fit elements are provided, adapted to cooperate with conjugated blocking elements provided on the engaging elements 40.i of the cartridge.

For example, the syringe 100 is provided with a pair of upper engaging holes 140.1, 140.2 of said counter-engaging means, arranged through the base 108 or the tubular body 102 in the area near the base 108, intended to engage with the upper engaging elements 40.1, 40.2 of the first small bag 18.

Preferably, moreover, the syringe 100 is provided with a pair of lower engaging holes 140.3, 140.4 of said counter-engaging means, arranged near the proximal end 103 of the tubular body 102, intended to engage with the lower engaging elements 40.3, 40.4 of the second small bag 22.

For example, at least one of said lower passing-through holes 140.3, 140.4 is arranged on the movable wall 130.

Typically, furthermore, the syringe 100 is provided with a pair of intermediate engaging holes 140.5, 140.6 of said counter-engaging means arranged through the tubular body 102 in an axially intermediate zone between the upper holes 140.1, 140.2 and the lower holes 140.3, 140.4; said intermediate holes 140.5, 140.6 are intended to engage with the intermediate engaging elements 40.5, 40.6 of the cartridge 10.

The base 108 is also provided with a light 111 passing through the axial depth, for inserting the needle 30.

In alternative, the base 108 is also provided with a radial channel 112, extending from the periphery to the centre of the base 108, passing through the thickness of the base and ending with the light 110.

The channel 112 opens up at the periphery of the base 108 in a corner position contained in the corner extension of the movable wall 130, so that while the needle 130 crosses radially the channel 112 to reach the light 110, the small bags 18, 22 car be accommodated in the space 120.

Preferably, furthermore, the needle-carrying component 32 can be blocked in the light 110 by shape coupling or for interference.

According to a preferred embodiment, the head 113 of the plunger 110 is dome-shaped, being convex towards the space 120 and preferably asymmetrical with respect to the main axis X, so as to perform a preferential squeezing on a side of the cartridge 10.

Preferably, furthermore, the syringe 100 has a bottom 122 at the distal end 106, in correspondence to the base 108, that is concave towards the space 120 and counter-shaped with respect to the head 113, so that it is complementary with it and facilitates the squeezing of the cartridge 10.

Figures 3, 4, 5:
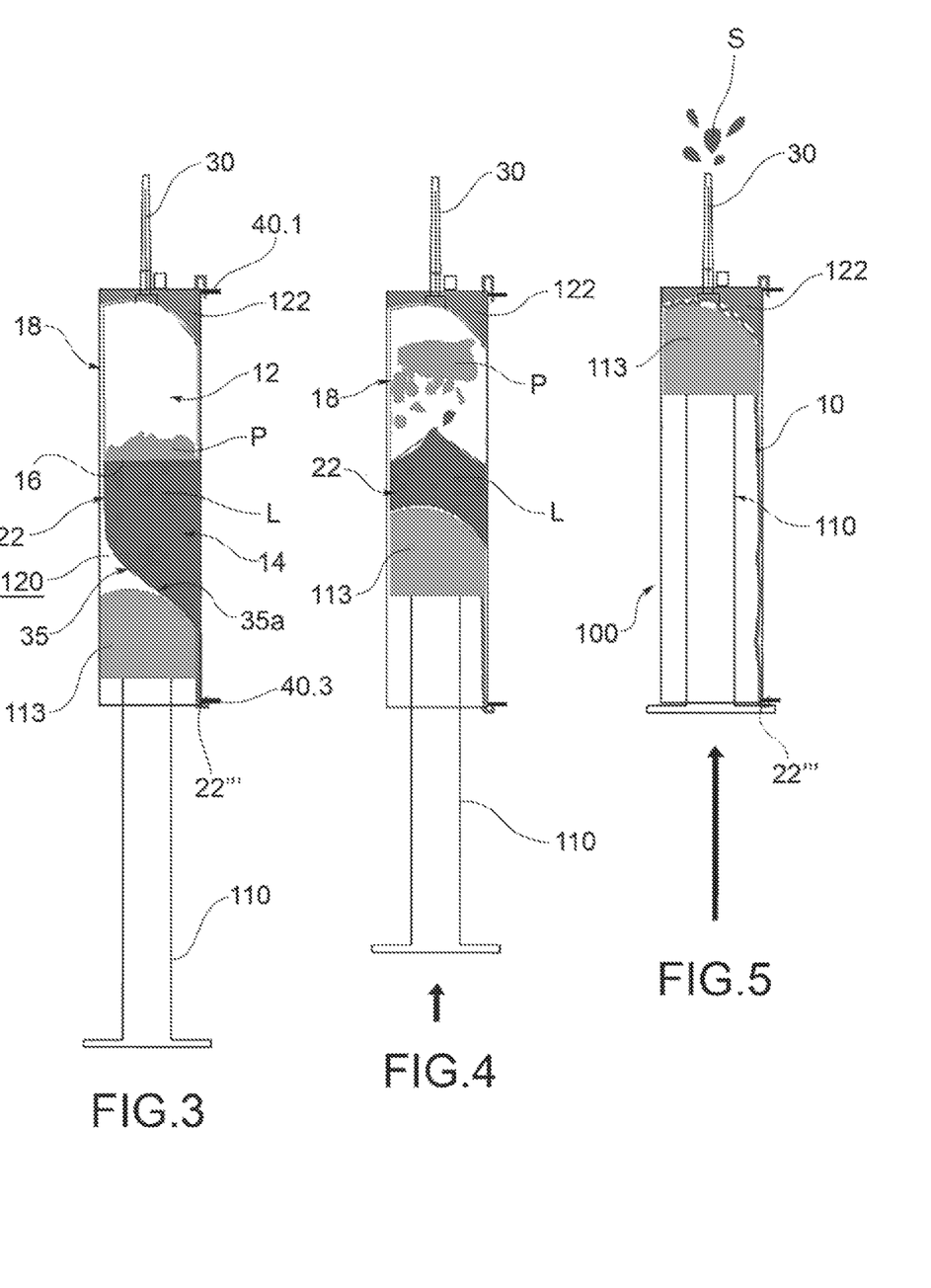
FIG. 3 shows a system formed by the cartridge accommodated in the syringe.
FIG. 4 shows the syringe-cartridge system in an intermediate using configuration.
FIG. 5 shows the syringe-cartridge system in a final using configuration.

In the usual functioning of the system according to the present invention, the syringe 100 is initially in a starting configuration wherein the plunger 110 is in a retracted position so as to determine an accomodating space 120 within the tubular body 102 adapted to accommodate the cartridge 10.

In such a configuration of the syringe 100, when the movable wall 130 is open, the cartridge 10 is inserted in the accomodating space 120, the needle 130 is disposed through the light 110 preferentially crossing the channel 112 and the cartridge is blocked to the syringe by engaging the engaging means of the cartridge with the counter-engaging means of the syringe.

In particular, each engaging element 40.$i$ is inserted in the respective engaging hole 140.$i$, so as to block the cartridge to the syringe.

Once the movable wall 130 is closed, the system is ready for use.

By performing an action on the plunger 110, the head 113 pushes on the small bag, being retained at the bottom by engaging the lower engaging elements 40.3, 40.4 with the respective lower engaging holes 140.3, 140.4.

The concave bottom 35 of the small bag cooperates with the dome-shaped head 113 of the plunger 110 and ensures a complete emptying of the chamber.

The plunger can advance until an advanced position wherein the head is in proximity of the bottom 122 and the cartridge is completely squeezed between the head 113 and said bottom 122 (FIG. 5).

The head 113 of the plunger squeezes completely the head surface 37, being dome-shaped, of the small bag, ensuring the complete emission of the solution.

When the injection is completed, the syringe can be opened and the empty cartridge is removed and set apart, for example to be inserted in a materials waste disposal process. On the contrary, the syringe can preferentially be reused.

According to the embodiment variant of FIG. 1, the squeezing of the second small bag 22 causes an increase of the pressure inside the second chamber 14, so much as to cause the breaking of the dividing wall 16 (FIG. 4).

Thus the liquid L pours into the first chamber 18, containing the powder P, and consequently the mixture to be injected is formed.

The concave bottom 35 of the small bag 22 cooperates with the dome-shaped head 113 of the plunger 110 and ensures a complete emptying of the liquid L.

The further pushing of the plunger 110 causes the squeezing of the first small bag 18 and the pouring out of the solution S to be injected through the needle 30, while the second small bag 18 is firmly anchored to the syringe by the upper engaging elements 40.1, 40.2 inserted and blocked in the upper engaging holes 140.1, 140.2.

The head 113 of the plunger 110 squeezes completely the head surface 37, being dome-shaped, of the first small bag 18, ensuring the complete emission of the solution.

In order to manufacture the cartridge according to the invention, the phases of a mechanized and constant methods of production are followed, as detailed hereinafter.

Figures 6, 7, 8:
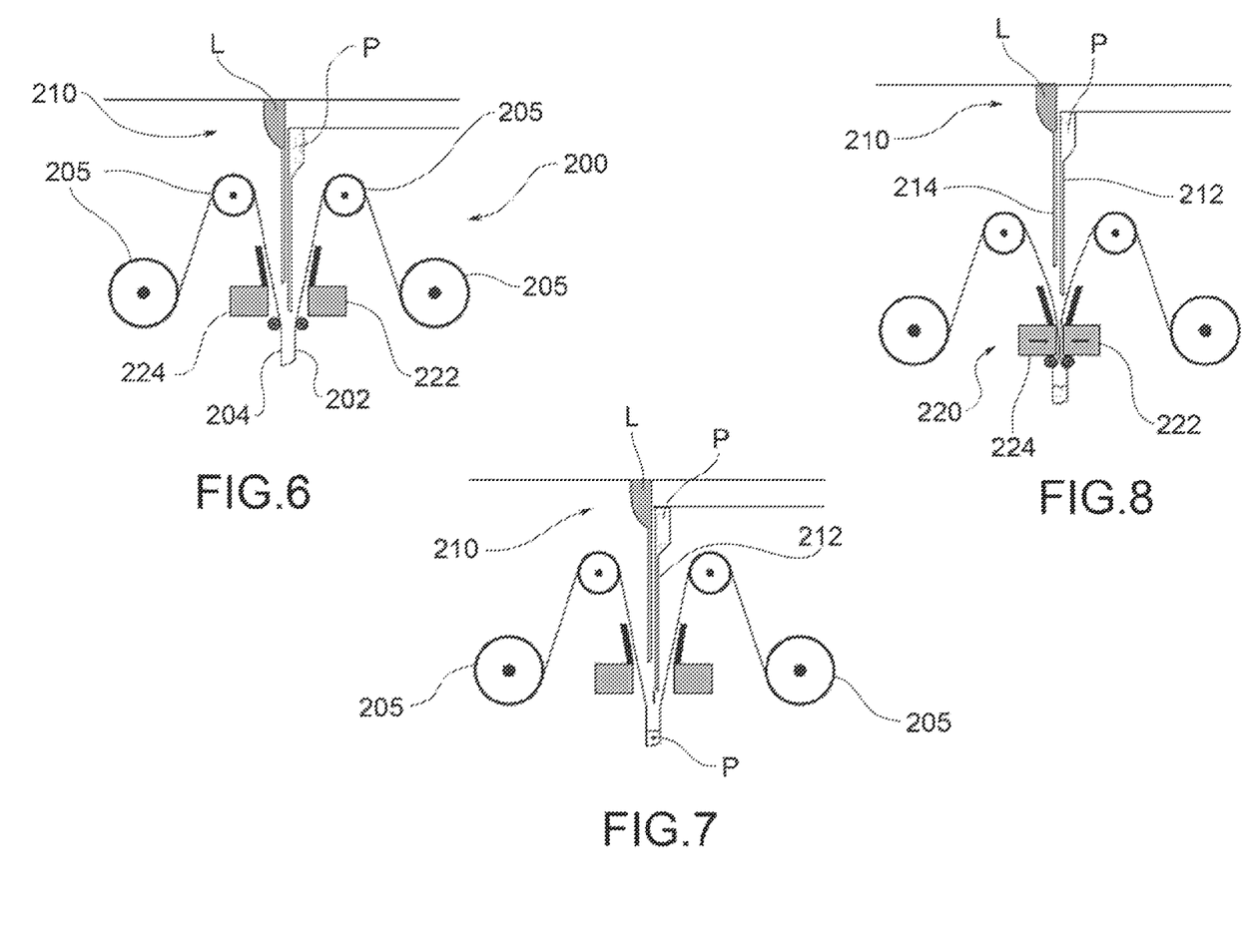
FIG. 6 schematically shows a machine for the manufacturing of the cartridge according to the invention.
FIGS. 7 to 10 show the phases of a method for manufacturing the cartridge according to the invention.

In a machine provided with a sterile chamber 200, a first continuous film strip 202 and a second continuous film strip 204, facing to each other, are made available.

For example, the machine is provided with rolls 205 for unrolling the films 202, 204

The machine is also provided with a dosing device 210 including at least two pipes 212, 214, respectively intended for dosing a controlled predetermined quantity of the mixture components, for example a predetermined quantity of powder P and a predetermined quantity of liquid L.

The machine is also provided with a joining device 220 to join the two films and form joining edges between them.

For example, said joining device 220 includes a welding apparatus including two welding heads 222, 224, being counter-posed, between which films 202, 204 pass.

In a first manufacturing phase, the front edge 20''' of the cartridge 10 is realized, for example by approaching the welding heads 222, 224, that staple the two films 202, 204 together and form said welded front edge 20'''(and possibly the lateral edges 20', 20'' of the small bag), forming a chamber that has an open side.

Thereafter, the dosing phase of the solution to be injected is performed (in the case of the embodiment variant of FIGS. 11 and 12) or of the first component of the solution, for example the dosing of the powder P (in the case of the embodiment variant of FIG. 1).

In the case of the embodiment variant of FIG. 1, for this purpose, a predefined quantity of powder P exits from the first pipe 212, possibly moved to an advanced position (FIG. 7).

Thereafter, having moved forward the films 202, 204, a phase for forming the breakable dividing wall 16, by initiating again the joining device, is performed.

For example, the welding heads 222, 224 approach each other, realizing a welding of the films 202, 204 that forms said dividing wall 16 (FIG. 8).

Thereafter, having moved forward the films 202, 204, a phase for dosing the second component of the solution, for example the dosing of the liquid L, is performed.

Figure 9:
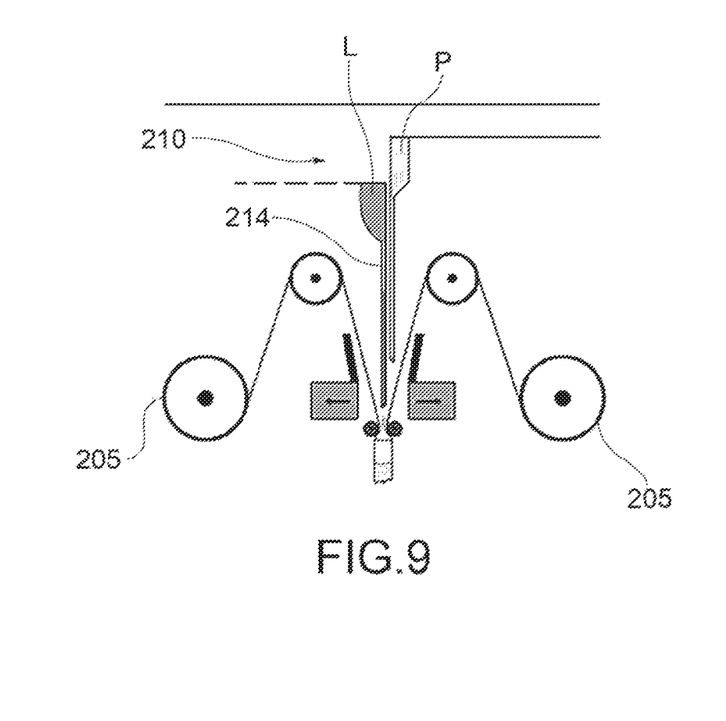

To this end, from the second pipe 214, possibly moved to an advanced position, a predefined quantity of liquid L exits (FIG. 9).

Figure 10:
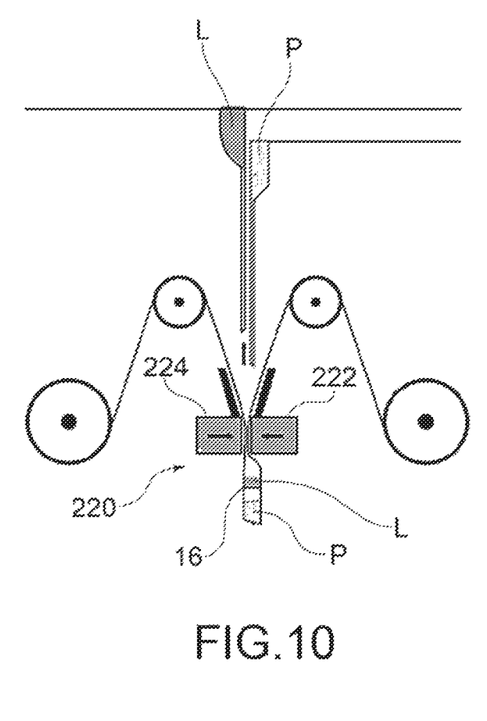

Finally, both for the variant of FIG. 1 and for the variant of FIG. 11, after possible moving back of the second pipe 214 or of both pipes 212, 214, the back edge of the small bag 22''' is formed, e.g. by approaching the welding heads 222, 224 (FIG. 10).

According to one embodiment, the engaging elements 40.$i$ of the cartridge are integrated in the film realized by the cartridge, for example in the form of tapes duly cut and with useless portions duly removed.

Alternatively, the engaging elements 40.$i$ are realized separately from the small bags 18, 22 of the cartridge and later applied to them, e.g. by bonding.

The concave and asymmetric bottom 35 and the head surface 37 are realized for example by thermoforming or by blow molding.

Another object of the present invention is an injection kit including the syringe and the cartridge 10. In a variant embodiment, the injection kit includes a syringe 100 and a plurality of cartridges 10.

Innovatively, the cartridge and the syringe according to the present invention overcome the drawbacks of the prior art in that they ensure a complete injection of the solution to be injected in order not to alter the dosage.

Advantageously, the geometry of the cartridge, basically in the internally concave head, together with the geometry of the syringe, basically in the dome-shaped head of the plunger, allow to empty completely the cartridge and ensure the dosage precision. In fact, no accumulation or stasis of the mixture or of the pharmaceutical substance remains in the little bag that is completely emptied.

Advantageously, the geometry of the cartridge, basically in the back part equipped with an asymmetric bend, serves to facilitate the sliding of the plunger and facilitates the release of the substance to inject.

Advantageously, the cartridge, the syringe and the method according to the present invention also allow to considerably reduce the manufacturing costs of the systems for the injection of a pharmaceutical mixture. In fact, the implementation of a cartridge by means of thin film strips eliminates the need for glass phials that contain the liquid component or components of the mixture.

Advantageously, furthermore, the constant manufacturing allows to considerably increase the manufacturing volumes and thus to further reduce the cost of the system.

Advantageously, furthermore, the system has a lower cost also for the final user since the syringe can be reused.

According to another advantageously aspect, the use of the system with cartridge with double chamber according to the invention is particularly safe for the patient, as it excludes any possibility of mistake in the dosing and mixing of the mixture components.

Furthermore, the use the system is particularly simple and safe since the cartridge is firmly held in position with respect to the syringe.

Obviously an expert in the field, in order to fulfil contingent requirements, may apply changes to the cartridge, to the syringe and to the above described method, being all contained for scope of protection as defined in the following claims.

The invention claimed is:

1. A cartridge for injecting a pharmaceutical solution when accommodated into a syringe, comprising at least a fully flexible bag extending along a main axis, said fully flexible bag comprising:
   a dome-shaped and outwardly convex head, wherein the head comprises a surface with an asymmetrical curvature;
   a first lateral wall and an opposing second lateral wall, the first and second lateral walls extending along the main axis and being connected along lateral edges, to the head, and to a bottom edge; wherein the head and the lateral walls are entirely made of flexible thin film walls;
   wherein the first and second lateral walls and the head define a chamber containing a pharmaceutical substance; and
   wherein the bag narrows from the first and second lateral walls to a top of the head.

2. The cartridge according to claim 1, a bottom portion of the first lateral wall comprising an outwardly concave bend.

3. The cartridge according to claim 2, wherein the bend is asymmetrical and formed by the first lateral wall narrowing to the bottom edge of the bag and the second lateral wall extending substantially parallel to the main axis.

4. The cartridge according to claim 1, wherein the bottom portion of the first lateral wall and/or the head surface are formed by thermoforming or by blow molding.

5. The cartridge according to claim 1, wherein the film is a monolayer film made of polyethylene, or the film is a multilayer film with an inner layer made of polyethylene.

6. The cartridge according to claim 1, comprising a needle protruding from the surface of the head, applied to said bag by a needle-carrying component.

7. The cartridge according to claim 1, wherein the bag comprises along the main axis, a first bag section and a second bag section internally divided by a dividing wall, the cartridge including engaging means for mechanically engaging and holding the cartridge in position in a syringe, wherein said engaging means protrude from the first bag section and/or from a second bag section and/or from the dividing wall.

8. The cartridge according to claim 1, comprising a first bag section having a first chamber containing a first component of the solution, and a second bag section having a second chamber containing a second component of the solution, said chambers being divided by a dividing wall that is breakable in order to mix the components.

9. The cartridge according to claim 8, wherein the first bag section includes lateral walls made of a thin film, being joined along joining edges to delimit the first chamber, the second bag section includes lateral walls made of a thin film, being joined along joining edges to delimit the second chamber, and wherein the dividing wall is made of a joining edge that is in common between the first and second bag sections.

10. The cartridge according to claim 1, including a single chamber containing an injectable solution.

* * * * *